(12) United States Patent
Rieger et al.

(10) Patent No.: US 7,666,506 B2
(45) Date of Patent: Feb. 23, 2010

(54) SURFACE-MODIFIED METAL OXIDES PREPARED BY PRECIPITATION IN THE PRESENCE OF A COPOLYMER HAVING N-VINYLAMIDE UNITS, PRODUCTION PROCESSES AND USE THEREOF IN COSMETIC PREPARATIONS

(75) Inventors: Jens Rieger, Ludwigshafen (DE); Jutta Kissel, Herxheim (DE); Valerie Andre, Ludwigshafen (DE); Nathalie Bouillo, Baden-Baden (DE)

(73) Assignee: BASF SE, Ludwigshafen (DE)

( * ) Notice: Subject to any disclaimer, the term of this patent is extended or adjusted under 35 U.S.C. 154(b) by 221 days.

(21) Appl. No.: 11/915,909

(22) PCT Filed: May 30, 2006

(86) PCT No.: PCT/EP2006/062732

§ 371 (c)(1),
(2), (4) Date: Nov. 29, 2007

(87) PCT Pub. No.: WO2006/128874

PCT Pub. Date: Dec. 7, 2006

(65) Prior Publication Data

US 2008/0193759 A1 Aug. 14, 2008

(30) Foreign Application Priority Data

Jun. 3, 2005 (DE) .................. 10 2005 025 972

(51) Int. Cl.
| | |
|---|---|
| B32B 5/16 | (2006.01) |
| B32B 9/04 | (2006.01) |
| B05D 3/00 | (2006.01) |
| B05D 7/00 | (2006.01) |
| A61K 8/18 | (2006.01) |

(52) U.S. Cl. ................ 428/407; 424/59; 424/69; 424/617; 424/641; 424/642; 424/646; 424/691; 427/215; 427/221

(58) Field of Classification Search .......... 428/403, 428/407; 427/212, 215, 221; 424/59, 69, 424/617, 641, 642, 646, 691
See application file for complete search history.

(56) References Cited

U.S. PATENT DOCUMENTS

| 5,593,781 | A | | 1/1997 | Nass et al. |
|---|---|---|---|---|
| 6,075,107 | A | * | 6/2000 | Kothrade et al. ............ 526/264 |
| 6,710,091 | B1 | * | 3/2004 | Womelsdorf et al. .......... 516/33 |
| 7,182,938 | B2 | * | 2/2007 | Andre et al. .................. 424/59 |
| 7,459,148 | B2 | * | 12/2008 | Nguyen-Kim et al. ... 424/70.11 |
| 2004/0054044 | A1 | * | 3/2004 | Bittner et al. ............... 524/261 |
| 2007/0243145 | A1 | * | 10/2007 | Andre et al. .................. 424/59 |
| 2007/0287757 | A1 | * | 12/2007 | Kuhnle et al. ................ 516/76 |

FOREIGN PATENT DOCUMENTS

| CA | 2520895 | 10/2004 |
|---|---|---|
| DE | 19907704 A1 | 8/2000 |
| DE | 10315363 | 10/2004 |
| JP | 04164814 | 6/1992 |
| JP | 07232919 | 9/1995 |
| WO | 9321127 | 10/1993 |
| WO | 0050503 | 8/2000 |
| WO | 2005105930 | 11/2005 |

OTHER PUBLICATIONS

L.Guo, et al., "Synthesis and Characterization of Poly(vinylpyrolidone)-Modified Zinc Oxide Nanoparticles," Chem. Mater., 2000, vol. 12, pp. 2268-2274.

* cited by examiner

*Primary Examiner*—H. (Holly) T Le
(74) *Attorney, Agent, or Firm*—Connolly Bove Lodge & Hutz LLP

(57) ABSTRACT

The present invention relates to surface-modified nanoparticulate metal oxides where the metal is chosen from the group consisting of aluminum, cerium, iron, titanium, zinc and zirconium, wherein the surface modification comprises a coating with a copolymer P comprising, as monomers,
A) 1 to 99 mol % of a N-vinylamide N-vinylpyrrolidone and
B) 99 to 1 mol % of a monomer comprising, per molecule, a free-radically polymerizable $\alpha,\beta$-ethylenically unsaturated double bond and an anionogenic and/or anionic group, with the proviso that the copolymer P must comprise no further monomers chosen from the group consisting of $C_8$-$C_{30}$-alkyl esters of monoethylenically unsaturated $C_3$-$C_8$-carboxylic acids, N-alkyl- or N,N-dialkyl-substituted amides of acrylic acid or of methacrylic acid with $C_8$-$C_{18}$-alkyl radicals, or vinyl esters of aliphatic $C_8$-$C_{30}$-carboxylic acids.

20 Claims, No Drawings

SURFACE-MODIFIED METAL OXIDES PREPARED BY PRECIPITATION IN THE PRESENCE OF A COPOLYMER HAVING N-VINYLAMIDE UNITS, PRODUCTION PROCESSES AND USE THEREOF IN COSMETIC PREPARATIONS

CROSS REFERENCE TO RELATED APPLICATIONS

This application is a National Phase of International Application No. PCT/LP2006/062732 filed on May 30, 2006, which claims priority to Application No. 1020050025972.3 filed in Germany on Jun. 3, 2005; the entire contents of which are hereby incorporated by reference.

The present invention relates to surface-modified nanoparticulate metal oxides, to processes for producing them and to their use as UV filters in cosmetic preparations.

Metal oxides are used for diverse purposes, thus, for example, as white pigment, as catalyst, as a constituent of antibacterial skin-protection ointments and as an activator for the vulcanization of rubber. Cosmetic sunscreens comprise finely divided zinc oxide or titanium dioxide as UV-absorbing pigments.

Within the scope of the present application, the term "nanoparticles" is used to refer to particles with an average diameter of from 5 to 10000 nm, determined by means of electron-microscopic methods.

Zinc oxide nanoparticles with particle sizes below about 30 nm are of potential suitability for use as UV absorbers in transparent organic-inorganic hybrid materials, plastics, paints and coatings. As well as this, a use for protecting UV-sensitive organic pigments is also possible.

Particles, particle aggregates or particle agglomerates of zinc oxide which are larger than about 30 nm lead to scattered-light effects and thus to an undesired decrease in transparency in the visible light region. For this reason, the redispersibility, i.e. the ability of the prepared zinc oxide nanoparticles to be converted to a colloidally disperse state, is an important prerequisite for the abovementioned applications.

Zinc oxide nanoparticles with particle sizes below about 5 nm exhibit, due to the size quantization effect, a blue shift of the absorption edge (L. Brus, J. Phys. Chem. (1986), 90, 2555-2560) and are therefore less suitable for use as UV absorbers in the UV-A region.

The preparation of metal oxides is known, for example of zinc oxide by dry and wet processes. The classic method of burning zinc, which is known as a dry process (e.g. Gmelin Volume 32, 8th edition, Supplementary volume, p. 772 ff.), produces aggregated particles with a broad size distribution. Although it is in principle possible to produce particle sizes in the submicrometer range by grinding processes, because the shear forces which can be achieved are too low, it is not possible to obtain dispersions with average particle sizes in the lower nanometer range from such powders. Particularly finely divided zinc oxide is produced primarily in a wet-chemical process by precipitation processes. The precipitation in aqueous solution generally produces hydroxide-containing and/or carbonate-containing materials which have to be converted thermally to zinc oxide. The thermal after-treatment has an adverse effect on the finely divided nature since the particles are here subjected to sintering processes which lead to the formation of micrometer-sized aggregates which can only be broken down incompletely to the primary particles by grinding.

Nanoparticulate metal oxides can be obtained, for example, by the microemulsion process. In this process, a solution of a metal alkoxide is added dropwise to a water-in-oil microemulsion. In the inverse micells of the microemulsion, the size of which is in the nanometer range, the hydrolysis of the alkoxides to the nanoparticulate metal oxide then takes place. The disadvantages of this process are, in particular, that the metal alkoxides are expensive starting materials, that emulsifiers have to additionally be used and that the preparation of the emulsions with particle sizes in the nanometer range is a complex process step.

DE 199 07 704 describes a nanoparticulate zinc oxide prepared via a precipitation reaction. In this process, the nanoparticulate zinc oxide is prepared via an alkaline precipitation starting from a zinc acetate solution. The zinc oxide which has been centrifuged off can be redispersed to give a sol by adding methylene chloride. The zinc oxide dispersions prepared in this way have the disadvantage that, due to a lack of surface modification, they do not have good long-term stability.

WO 00/50503 describes zinc oxide gels which comprise nanoparticulate zinc oxide particles with a particle diameter of $\leq 15$ nm and which are redispersible to give sols. In this process, the precipitations produced by basic hydrolysis of a zinc compound in alcohol or in an alcohol/water mixture are redispersed by adding dichloromethane or chloroform. A disadvantage here is that in water or in aqueous dispersants, stable dispersions are not obtained.

In the publication from Chem. Mater. 2000, 12, 2268-74 "Synthesis and Characterization of Poly(vinylpyrrolidone)-Modified Zinc Oxide Nanoparticles" by Lin Guo and Shihe Yang, wurtzite zinc oxide nanoparticles are surface-coated with polyvinylpyrrolidone. The disadvantage here is that zinc oxide particles coated with polyvinylpyrrolidone are not dispersible in water.

WO 93/21127 describes a process for the preparation of surface-modified nanoparticulate ceramic powders. In this process, a nanoparticulate ceramic powder is surface-modified by applying a low molecular weight organic compound, for example propionic acid. This process cannot be used for the surface modification of zinc oxide since the modification reactions are carried out in aqueous solution and zinc oxide dissolves in aqueous organic acids. This process can therefore not be used for producing zinc oxide dispersions; moreover, in this application, zinc oxide is also not specified as a possible starting material for nanoparticulate ceramic powders.

JP-A-04 164 814 describes a process which leads to finely divided ZnO as a result of precipitation in aqueous medium at elevated temperature even without thermal after-treatment. The average particle size stated is 20-50 nm with no indication of the degree of agglomeration. These particles are relatively large. Even if agglomeration is minimal, this leads to scatter effects which are undesired in transparent applications.

JP-A-07 232 919 describes the preparation of ZnO particles of 5 to 10000 nm in size from zinc compounds through reaction with organic acids and other organic compounds, such as alcohols, at elevated temperature. The hydrolysis takes place here such that the byproducts which form (esters of the acids used) can be distilled off. The process allows the preparation of ZnO powders which are redispersible by virtue of prior surface modification. However, on the basis of the disclosure of this application, it is not possible to produce particles with an average diameter of <15 nm. Accordingly, in the examples listed in the application, 15 nm is specified as the smallest average primary particle diameter.

Metal oxides hydrophobicized with organosilicon compounds are described, inter alia, in DE 33 14 741 A1, DE 36 42 794 A1 and EP 0 603 627 A1 and also in WO 97/16156.

These metal oxides coated with silicone compounds, for example zinc oxide or titanium dioxide, have the disadvantage that oil-in-water or water-in-oil emulsions prepared therewith do not always have the required pH stability.

In addition, incompatibilities of various metal oxides coated with silicone compounds with one another are often observed, which may lead to undesired aggregate formations and to flocculations of the different particles.

The object of the present invention was therefore to provide nanoparticulate metal oxides which permit the preparation of stable nanoparticulate dispersions in water or polar organic solvents and also in cosmetic oils. Irreversible aggregation of the particles should, if possible, be avoided so that a complex grinding process can be avoided.

This object was achieved by surface-modified nanoparticulate metal oxides, where the metal is chosen from the group consisting of aluminum, cerium, iron, titanium, zinc and zirconium, wherein the surface modification a coating with a copolymer P comprising, as monomers, A) 1 to 99 mol %, preferably 50 to 99 mol %, particularly preferably 75 to 99 mol %, of a N-vinylamide and B) 99 to 1 mol %, preferably 50 to 1 mol %, particularly preferably 25 to 1 mol %, of a monomer comprising, per molecule, one free-radically polymerizable α,β-ethylenically unsaturated double bond and one anionogenic and/or anionic group, with the proviso that the copolymer P must comprise no further monomers chosen from the group consisting of $C_8$-$C_{30}$-alkyl esters of monoethylenically unsaturated $C_3$-$C_8$-carboxylic acids, N-alkyl- or N,N-dialkyl-substituted amides of acrylic acid or of methacrylic acid with $C_8$-$C_{18}$-alkyl radicals, or vinyl esters of aliphatic $C_8$-$C_{30}$-carboxylic acids.

The monomer A) is chosen from the N-vinylamide group of substances. Here, these may either be open-chain or cyclic N-vinylamides (N-vinyllactams). The monomers chosen generally have 2 to 15 carbon atoms, preferably 2 to 10 carbon atoms. N-Vinylamides and N-vinyllactams which may be mentioned by way of example are those which are characterized by the following formula (I):

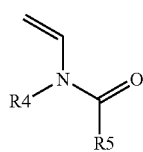

(I)

in which

R4, R5 independently of one another are H or $C_1$-$C_6$-alkyl or together can form a 4- to 8-membered cycle, which may be saturated or mono- or polyunsaturated and can, if appropriate, carry further substituents.

Suitable open-chain compounds of this type are, for example, N-vinylformamide, N-vinyl-N-methylformamide, N-vinyl-N-ethylformamide, N-vinyl-N-propylformamide, N-vinyl-N-isopropylformamide, N-vinyl-N-n-butylformamide, N-vinyl-N-isobutylformamide, N-vinyl-N-t-butylformamide, N-vinyl-N-n-pentylformamide, N-vinyl-N-n-hexylformamide, N-vinylacetamide, N-vinyl-N-methylacetamide, N-vinyl-N-ethylacetamide, N-vinylpropionamide, N-vinyl-N-methylpropionamide and N-vinylbutyramide. N-vinylformamide and N-vinyl-N-methylacetamide are particularly preferred.

Of the cyclic N-vinylamides, the N-vinyllactams, mention may be made by way of example of N-vinylpyrrolidone, N-vinylpiperidone and N-vinylcaprolactam. According to the invention, preference is given to using N-vinylpyrrolidone, while preference is given to using N-vinylformamide from the open-chain N-vinylamides. Copolymers of, for example, N-vinylformamide and N-vinylpyrrolidone, which may be present in the copolymer in any desired ratio, can also be used in a manner according to the invention.

The monomers A) can be used as they are or as mixtures with one another.

The monomer B) comprises, per molecule, one free-radically polymerizable α,β-ethylenically unsaturated double bond and one anionogenic and/or anionic group per molecule.

Preference is given to the compounds B) chosen from monoethylenically unsaturated carboxylic acids, sulfonic acids, phosphonic acid and mixtures thereof.

Monoethylenically unsaturated carboxylic acids are understood as meaning monoethylenically unsaturated mono- and dicarboxylic acids having 3 to 25, preferably 3 to 8, carbon atoms. Examples thereof are acrylic acid, methacrylic acid, dimethacrylic acid, ethacrylic acid, α-chloroacrylic acid, maleic acid, methylenemalonic acid, allylacetic acid, vinylacetic acid, crotonic acid, citraconic acid, mesaconic acid, glutaconic acid, aconitic acid, fumaric acid and itaconic acid. From this group of monomers, preference is given to using acrylic acid, methacrylic acid, maleic acid or mixtures of the specified carboxylic acids. The monoethylenically unsaturated carboxylic acids can be used in the form of the free acid and—if present—the anhydrides or in partially or completely neutralized form during the copolymerization. In order to neutralize these monomers, preference is given to using alkali metal or alkaline earth metal bases, ammonia or amines, e.g. sodium hydroxide solution, potassium hydroxide solution, sodium carbonate, potassium carbonate, sodium hydrogencarbonate, magnesium oxide, calcium hydroxide, calcium oxide, gaseous or aqueous ammonia, triethylamine, ethanolamine, diethanolamine, triethanolamine, morpholine, diethylenetriamine or tetraethylenepentamine.

The monomers B) also include the half-esters of monoethylenically unsaturated dicarboxylic acids having 4 to 10, preferably 4 to 6, carbon atoms, e.g. of maleic acid, such as monomethyl maleate.

The monomers B) also include monoethylenically unsaturated sulfonic acids and phosphonic acids, for example vinylsulfonic acid, allylsulfonic acid, methallylsulfonic acid, sulfoethyl acrylate, sulfoethyl methacrylate, sulfopropyl acrylate, sulfopropyl methacrylate, 2-hydroxy-3-acryloxypropylsulfonic acid, 2-hydroxy-3-methacryloxypropylsulfonic acid, styrenesulfonic acid, 2-acrylamido-2-methylpropanesulfonic acid, vinylphosphonic acid, allylphosphonic acid and acrylamidomethanepropanephosphonic acid.

The monomers B) can be used as they are or as mixtures with one another.

Preferably, component B) is chosen from acrylic acid, methacrylic acid, ethacrylic acid, α-chloroacrylic acid, crotonic acid, maleic acid, maleic anhydride, fumaric acid, itaconic acid, citraconic acid, mesaconic acid, glutaconic acid, aconitic acid and mixtures thereof.

Component B) is particularly preferably chosen from acrylic acid, methacrylic acid, maleic anhydride and mixtures thereof, very particular preference being given to acrylic acid.

Copolymer P to be used particularly advantageously as coating for the surface-modified nanoparticulate metal oxides according to the invention comprises 75 to 99 mol % of N-vinylpyrrolidone and 1 to 25 mol % of acrylic acid.

Additional comonomers for the polymer P which are excluded are:

a)

$C_8$-$C_{30}$-Alkyl esters of monoethylenically unsaturated $C_3$-$C_8$-carboxylic acids, such as acrylic acid, methacrylic acid, dimethacrylic acid, ethacrylic acid, maleic acid, citraconic acid, methylenemalonic acid, allylacetic acid, vinylacetic acid, crotonic acid, fumaric acid, mesaconic acid or itaconic acid. The alkyl radicals also comprise cycloalkyl radicals. Further comonomers which are excluded are, for example, octyl acrylate, 2-ethylhexyl acrylate, 2-ethylhexyl methacrylate, nonyl acrylate, decyl acrylate, lauryl acrylate, myristyl acrylate, cetyl acrylate, stearyl acrylate, oleyl acrylate, behenyl acrylate, hexyl methacrylate, octyl methacrylate, nonyl methacrylate, decyl methacrylate, lauryl methacrylate, myristyl methacrylate, cetyl methacrylate, stearyl methacrylate, oleyl methacrylate, behenyl methacrylate or tert-butylcyclohexyl acrylate.

b)

N-Alkyl- or N,N-dialkyl-substituted carboxamides of acrylic acid or of methacrylic acid, where the alkyl radicals are $C_8$-$C_{18}$-alkyl or cycloalkyl radicals, for example N-stearylacrylamide, N-stearylmethacrylamide, N-octylacrylamide, N,N-dioctylacrylamide, N,N-dioctylmethacrylamide, N-cetylacrylamide, N-cetylmethacrylamide, N-dodecyl-acrylamide, N-dodecylmethacrylamide, N-myristylacrylamide, 2-ethylhexylacrylamide.

c)

Vinyl esters of aliphatic carboxylic acids ($C_8$-$C_{30}$-carboxylic acids), for example vinyl esters of octanoic acid, nonanoic acid, decanoic acid, undecanoic acid, lauric acid, tridecanoic acid, myristic acid, palmitic acid, stearic acid, arachinic acid or behenic acid or of oleic acid.

Further comonomers C) which can be used are the following copolymerizable monomers (or else mixtures thereof) in amounts of from 0 to 39 mol %, preferably 1 to 20 mol %, particularly preferably 2 to 10 mol %.

Suitable comonomers C) are, for example, the $C_1$-$C_7$-alkyl esters, $C_1$-$C_7$-alkyamides and nitriles of the mono- and dicarboxylic acids given above (as monomer B), e.g. methyl acrylate, ethyl acrylate, methyl methacrylate, ethyl methacrylate, hydroxyethyl acrylate, hydroxypropyl acrylate, hydroxybutyl acrylate, hydroxyethyl methacrylate, hydroxypropyl methacrylate, hydroxyisobutyl acrylate, hydroxyisobutyl methacrylate, monomethyl maleate, dimethyl maleate, monoethyl maleate, diethyl maleate, acrylamide, methacrylamide, N,N-dimethylacrylamide, N-tert-butylacrylamide, N-diethylacrylamide, N-isopropylacrylamide, acrylonitrile, methacrylonitrile.

Further suitable copolymerizable compounds C) are also N-vinylamines, in particular N-vinylamine, and N-vinylimines, such as, for example, N-vinylimidazole, N-vinyl-2-methylimidazole, N-vinyl-4-methylimidazole, preferably N-vinylimidazole.

Further suitable monomers C) are also vinyl esters of aliphatic carboxylic acids ($C_1$-$C_7$-carboxylic acids), for example vinyl acetate, vinyl propionate. Further suitable monomers C are, moreover, the vinyl ethers, for example octadecyl vinyl ether.

It is also possible to use cationic monomers as monomer C). Preferably, the cationogenic or cationic groups of these monomers are nitrogen-containing groups, such as primary, secondary and tertiary amino groups, and quaternary ammonium groups. Preferably, the nitrogen-containing groups are tertiary amino groups or quaternary ammonium groups. Charged cationic groups can be produced from the amine nitrogens either by protonation, e.g. with monohydric or polyhydric carboxylic acids, such as lactic acid or tartaric acid, or mineral acids, such as phosphoric acid, sulfuric acid and hydrochloric acid, or by quaternization, e.g. with alkylating agents, such as $C_1$-$C_4$-alkyl halides or sulfates. Examples of such alkylating agents are ethyl chloride, ethyl bromide, methyl chloride, methyl bromide, dimethyl sulfate and diethyl sulfate. In a preferred embodiment, the monomers C) are used in charged form for the polymerization.

Suitable compounds C) are, for example, the esters of α,β-ethylenically unsaturated mono- and dicarboxylic acids with amino alcohols. Preferred amino alcohols are $C_2$-$C_{12}$-amino alcohols which are $C_1$-$C_8$-dialkylated on the amine nitrogen. Suitable acid components of these esters are, for example, acrylic acid, methacrylic acid, fumaric acid, maleic acid, itaconic acid, crotonic acid, maleic anhydride, monobutyl maleate and mixtures thereof. Preference is given to using acrylic acid, methacrylic acid and mixtures thereof. Preference is given to N,N-dimethylaminomethyl(meth)acrylate, N,N-dimethylaminoethyl (meth)acrylate, N,N-diethylaminoethyl(meth)acrylate, N,N-dimethylaminopropyl (meth)acrylate, N,N-diethylaminopropyl(meth)acrylate and N,N-dimethylaminocyclohexyl (meth)acrylate.

Suitable monomers C) are also the amides of the abovementioned α,β-ethylenically unsaturated mono- and dicarboxylic acids with diamines which have at least one primary or secondary amino group. Preference is given to diamines which have one tertiary and one primary or secondary amino group. As monomers c), preference is given to using N-[2-(dimethylamino)ethyl]acrylamide, N-[2-(dimethylamino)ethyl]methacrylamide, N-[3-(dimethylamino)propyl]acrylamide, N-[3-(dimethylamino)propyl]methacrylamide, N-[4-(dimethylamino)butyl]acrylamide, N-[4-(dimethylamino)butyl]methacrylamide, N-[2-(diethylamino)ethyl]acrylamide, N-[4-(dimethylamino)cyclohexyl]acrylamide, N-[4-(dimethylamino)cyclohexyl]methacrylamide etc. Particular preference is given to using N-[3-(dimethylamino)propyl]acrylamide and/or N-[3-(dimethylamino)propyl]methacrylamide.

Suitable monomers C) are also N,N-diallylamines and N,N-diallyl-N-alkylamines and acid addition salts and quaternization products thereof. Alkyl here is preferably $C_1$-$C_{24}$-alkyl. Preference is given to N,N-diallyl-N-methylamine and N,N-diallyl-N,N-dimethylammonium compounds, such as, for example, the chlorides and bromides.

Suitable monomers C) are also of component vinyl- and allyl-substituted nitrogen heterocycles, such as N-vinylimidazole, N-vinyl-2-methylimidazole, vinyl- and allyl-substituted heteroaromatic compounds, such as 2- and 4-vinylpyridine, 2- and 4-allylpyridine, and the salts thereof.

Preferred monomers C) are the N-vinylimidazole derivatives of the general formula (II) in which $R^1$ to $R^3$ is hydrogen, $C_1$-$C_4$-alkyl or phenyl (II)

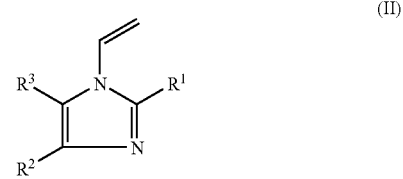

Examples of compounds of the general formula (II) are given in Table 1 below:

TABLE 1

| $R^1$ | $R^2$ | $R^3$ |
|---|---|---|
| H | H | H |
| Me | H | H |
| H | Me | H |
| H | H | Me |
| Me | Me | H |
| H | Me | Me |
| Me | H | Me |
| Ph | H | H |
| H | Ph | H |
| H | H | Ph |
| Ph | Me | H |
| Ph | H | Me |
| Me | Ph | H |
| H | Ph | Me |
| H | Me | Ph |
| Me | H | Ph |

Me = methyl
Ph = phenyl

Preferred examples of monomers C) are 3-methyl-1-vinylimidazolium chloride and methosulfate, dimethyidiallylammonium chloride, and N,N-dimethylaminoethyl methacrylate and N-[3-(dimethylamino)propyl]methacrylamide which have been quaternized by methyl chloride, dimethyl sulfate or diethyl sulfate.

Particularly preferred monomers C) are 3-methyl-1-vinylimidazolium chloride and methosulfate and dimethyldiallylammonium chloride (DADMAC), very particular preference being given to 3-methyl-1-vinylimidazolium chloride and methosulfate.

A further copolymerizable monomer C) which may be mentioned is diallylammonium chloride.

The specified monomers C) can be used according to the invention either individually or in the form of mixtures of two or more of the specified compounds.

The copolymers are prepared by known processes, e.g. solution, precipitation or inverse suspension polymerization using compounds which form free radicals under the polymerization conditions.

The polymerization temperatures are usually in the range from 30 to 200, preferably 40 to 110° C. Suitable initiators are, for example, azo and peroxy compounds, and the customary redox initiator systems, such as combinations of hydrogen peroxide and reductive compounds, e.g. sodium sulfite, sodium bisulfite, sodium formaldehyde sulfoxylate and hydrazine.

The copolymers P have K values of at least 7 to 130, preferably 10 to 100, particularly preferably 10 to 50. The K values are determined in accordance with H. Fikentscher, Cellulose-Chemie, Volume 13, 58 to 64 and 71 to 74 (1932) in aqueous 0.1 M NaCl solution at 25° C. for polymer concentrations which are between 0.1% and 5%, preferably 1%, depending on the K value range.

A preferred embodiment of the metal oxides according to the invention is one in which the metal oxide particles have an average primary particle diameter of from 5 to 10000 nm, preferably from 10 to 200 nm, particularly preferably from 10 to 50 nm, particle diameter determined by means of scanning and transmissions electron microscopy.

For the purposes of the present invention, preferred metal oxides to be mentioned are titanium dioxide and zinc oxide, particularly preferably zinc oxide.

The invention is based on the finding that by virtue of a surface modification of nanoparticulate metal oxides with copolymer P it is possible to achieve long-term stability of dispersions of the surface-modified metal oxides, in particular in cosmetic preparations without undesired changes in the pH during storage of these preparations.

The invention further provides a process for the preparation of a surface-modified nanoparticulate metal oxide where the metal is chosen from the group consisting of aluminum, cerium, iron, titanium, zinc and zirconium, by a. precipitation of the metal oxide from an aqueous or alcoholic solution of one of its metal salts,
b. separating off the precipitated metal oxide from the aqueous or alcoholic reaction mixture and
c. subsequent drying of the metal oxide, wherein the precipitation of the metal oxide in process step a. takes place in the presence of a copolymer P which comprises, as monomers, A) 1 to 99 mol % of a N-vinylamide and
B) 99 to 1 mol % of a monomer comprising, per molecule, one free-radically polymerizable α,β-ethylenically unsaturated double bond and one anionogenic and/or anionic group, with the proviso that the copolymer P must comprise no further monomers chosen from the group consisting of $C_8$-$C_{30}$-alkyl esters of monoethylenically unsaturated $C_3$-$C_8$-carboxylic acids, N-alkyl- or N,N-dialkyl-substituted amides of acrylic acid or of methacrylic acid with $C_8$-$C_{18}$-alkyl radicals, or vinyl esters of aliphatic $C_8$-$C_{30}$-carboxylic acids.

The metal salts in process step a. may be metal halides, acetates, sulfates or nitrates. Preferred metal salts here are halides, for example zinc(II) chloride or titanium tetrachloride, and nitrates, for example zinc(II) nitrate, and acetates, for example zinc(II) acetate.

Alcoholic solution is understood as meaning, for example, a methanolic or ethanolic solution or else a mixture of water and an alcohol, for example methanol, ethanol or isopropanol.

The precipitation of the metal oxide in process step a. can take place at a temperature in the range from 20° C. to 100° C., preferably in the range from 25° C. to 40° C.

Depending on the metal salt used, the precipitation can be carried out at a pH in the range from 3 to 13. In the case of zinc oxide, the pH during the precipitation is in the range from 7 to 11.

The concentration of the metal salts is usually in the range from 0.05 to 1 mol/l, preferably in the range from 0.1 to 0.5 mol/l, particularly preferably in the range from 0.2 to 0.4 mol/l.

The precipitation time is generally 0.2 to 8 hours, preferably 0.2 to 7 hours, particularly preferably 0.5 to 5 hours, very particularly preferably 1 to 2 hours.

With regard to the definition of the copolymer P used in the process according to the invention as surface coating, both in the general embodiment and also preferred embodiment, reference may be made to the description given at the start.

The present invention provides, in particular, a process for the preparation of surface-modified nanoparticulate zinc oxide by a. precipitation of the zinc oxide from an aqueous solution of zinc(II) chloride, zinc(II) nitrate or zinc(II) acetate at a temperature in the range from 25 to 40° C. and a pH in the range from 7 to 11 in the presence of an alkali metal hydroxide, b. separating off the precipitated zinc oxide from the aqueous reaction mixture and c. subsequent drying, wherein the precipitation of the zinc oxide takes place in process step a. in the presence of copolymer P.

The precipitation of the zinc oxide in process step a. can take place, for example, through the metered addition of an aqueous solution of a mixture of copolymer P and an alkali metal hydroxide or ammonium hydroxide, in particular NaOH, to the aqueous solution of zinc(II) chloride, zinc(II) nitrate or zinc(II) acetate or through the simultaneous metered addition in each case of an aqueous solution of zinc (II) chloride, zinc(II) nitrate or zinc(II) acetate and an aqueous solution of an alkali metal hydroxide or ammonium hydroxide, in particular NaOH, to an aqueous solution of the copolymer P.

The precipitated metal oxide can be separated off from the aqueous reaction mixture in a manner known per se, for example by filtration or centrifugation.

The filter cake obtained can be dried in a manner known per se, for example in a drying cabinet at temperatures between 40 and 100° C., preferably between 50 and 70° C., under atmospheric pressure to constant weight.

The present invention further provides a cosmetic composition which comprises a zinc oxide surface-coated according to the invention or a zinc oxide dispersion.

The present invention further provides the use of surface-modified metal oxide, in particular titanium dioxide or zinc oxide, which are prepared by the process according to the invention:

for UV protection as antimicrobial active ingredient

According to a preferred embodiment of the present invention, the surface-modified metal oxide, in particular titanium dioxide or zinc oxide is redispersible in a liquid medium and forms stable dispersions. This is particularly advantageous because the dispersions prepared from the zinc oxide according to the invention do not have to be dispersed again prior to further processing, but can be processed directly.

According to a preferred embodiment of the present invention, the surface-modified metal oxide is redispersible in polar organic solvents and forms stable dispersions. This is particularly advantageous since this enables uniform incorporation, for example, into plastics or films.

According to a further preferred embodiment of the present invention, the surface-modified metal oxide is redispersible in water and forms stable dispersions therein. This is particularly advantageous since this opens up the possibility of using the material according to the invention, for example, in cosmetic formulations, where the omission of organic solvents is a great advantage. Also conceivable are mixtures of water and polar organic solvents.

According to a preferred embodiment of the present invention, the surface-modified metal oxide particles have a diameter of from 10 to 200 nm. This is particularly advantageous since good redispersibility is ensured within this size distribution.

According to a particularly preferred embodiment of the present invention, the metal oxide nanoparticles have a diameter of from 10 to 50 nm. This size range is particularly advantageous since following the redispersion of such zinc oxide nanoparticles, the resulting dispersions are transparent and thus, for example, do not affect the coloring when added to cosmetic formulations. Moreover, this also gives rise to the possibility of use in transparent films.

If the metal oxides, in particular titanium dioxide or zinc oxide, are to be used as UV absorbers, it is advisable to use particles with a diameter of more than 5 nm since below this limit the absorption edge shifts into the short-wave range (L. Brus, J. Phys., Chem. (1986), 90, 2555-2560).

The present invention further provides a cosmetic composition which comprises a metal oxide, in particular titanium dioxide and/or zinc oxide, surface-modified according to the invention. This is particularly advantageous since, on account of the fine distribution of the metal oxide particles, in particular of the zinc oxide particles, these can develop their skin-calming effect more effectively.

A further advantage is that when being applied to, for example, the skin, due to the small particle size, no rubbing effect arises, but a soft application is possible, which brings about a pleasant feel on the skin.

According to a further embodiment of the cosmetic composition, this serves for the care or protection of the skin, in particular for sun protection or for care upon exposure to sunlight and is in the form of an emulsion, a dispersion, a suspension, an aqueous surfactant preparation, a milk, a lotion, a cream, a balsam, an ointment, a gel, granules, a powder, a stick preparation, such as, for example, a lipstick, a foam, an aerosol or a spray. Such formulations are highly suitable for topical preparations. Suitable emulsions are oil-in-water emulsions and water-in-oil emulsions or microemulsions. This is particularly advantageous since, by using them in sunscreens, the UV-absorbing and the skin-calming effect for example of zinc oxide can be utilized at the same time. Moreover, the metal oxides surface-modified according to the invention are exceptionally suitable for use in sunscreens since the particles can be prepared in a size which appears to be transparent to the human eye. As a result, no white haze arises on the skin during use.

A further advantage is the fact that zinc oxide in particular is a UV broadband filter whose UV absorption behavior allows a sunscreen to be provided which no longer requires further chemical UV filter substances. As a result, the danger of skin irritations or allergic reactions through decomposition products of chemical filters or through these substances themselves can be avoided, which significantly increases the general compatibility of a sunscreen formulated in this way. Generally, the cosmetic composition is used for topical application on the skin. Here, topical preparations are understood as meaning those preparations which are suitable for applying the active ingredients to the skin in a fine distribution and preferably in a form which can be absorbed by the skin. Of suitability for this purpose are, for example, aqueous and aqueous-alcoholic solutions, sprays, foams, foam aerosols, ointments, aqueous gels, emulsions of the O/W or W/O type, microemulsions or cosmetic stick preparations.

According to a preferred embodiment of the cosmetic composition according to the invention, the composition comprises a carrier. Preferred carriers are water, a gas, a water-based liquid, an oil, a gel, an emulsion or microemulsion, a dispersion or a mixture thereof. The specified carriers exhibit good skin compatibility. Aqueous gels, emulsions or microemulsions are particularly advantageous for topical preparations.

Emulsifiers which can be used are nonionogenic surfactants, zwitterionic surfactants, ampholytic surfactants or anionic emulsifiers. The emulsifiers can be present in the composition according to the invention in amounts of from 0.1 to 10% by weight, preferably 1 to 5% by weight, based on the composition.

The nonionogenic surfactant used may, for example, be a surfactant from at least one of the following groups:

addition products of from 2 to 30 mol of ethylene oxide and/or 0 to 5 mol of propylene oxide onto linear fatty alcohols having 8 to 22 carbon atoms, onto fatty acids having 12 to 22 carbon atoms and onto alkylphenols having 8 to 15 carbon atoms in the alkyl group;

$C_{12/18}$-fatty acid mono- and diesters of addition products of from 1 to 30 mol of ethylene oxide onto glycerol;

glycerol mono- and diesters and sorbitan mono- and diesters of saturated and unsaturated fatty acids having 6 to 22 carbon atoms and ethylene oxide addition products thereof;

alkyl mono- and oligoglycosides having 8 to 22 carbon atoms in the alkyl radical and ethoxylated analogs thereof;

addition products of from 15 to 60 mol of ethylene oxide onto castor oil and/or hydrogenated castor oil;

polyol and, in particular, polyglycerol esters, such as, for example, polyglycerol polyricinoleate, polyglycerol poly-12-hydroxystearate or polyglycerol dimerate. Likewise of suitability are mixtures of compounds of two or more of these classes of substances;

addition products of from 2 to 15 mol of ethylene oxide onto castor oil and/or hydrogenated castor oil;

partial esters based on linear, branched, unsaturated or saturated $C_{6/22}$-fatty acids, ricinoleic acid, and 12-hydroxystearic acid and glycerol, polyglycerol, pentaerythritol, dipentaerythritol, sugar alcohols (e.g. sorbitol), alkylglucosides (e.g. methyl glucoside, butyl glucoside, lauryl glucoside), and polyglucosides (e.g. cellulose);

mono-, di- and trialkyl phosphates, and mono-, di- and/or tri-PEG-alkyl phosphates and salts thereof;

wool wax alcohols;

polysiloxane-polyalkyl-polyether copolymers and corresponding derivatives;

mixed esters of pentaerythritol, fatty acids, citric acid and fatty alcohol according to German patent 1165574 and/or mixed esters of fatty acids having 6 to 22 carbon atoms, methylglucose and polyols, preferably glycerol or polyglycerol, and polyalkylene glycols;

betaines.

In addition, zwitterionic surfactants can be used as emulsifiers. Zwitterionic surfactants is the term used to refer to those surface-active compounds which carry in the molecule at least one quaternary ammonium group and at least one carboxylate or one sulphonate group. Particularly suitable zwitterionic surfactants are the so-called betaines, such as the N-alkyl-N,N-dimethylammonium glycinates, for example cocoalkyldimethylammonium glycinate, N-acylaminopropyl-N,N-dimethylammonium glycinate, for example cocoacylaminopropyldimethylammonium glycinate, and 2-alkyl-3-carboxymethyl-3-hydroxyethylimidazolines having in each case 8 to 18 carbon atoms in the alkyl or acyl group, and cocoacylaminoethylhydroxyethyl carboxymethylglycinate. Of particular preference is the fatty acid amide derivative known under the CTFA name Cocamidopropyl Betaine.

Likewise suitable emulsifiers are ampholytic surfactants. Ampholytic surfactants are understood as meaning those surface-active compounds which, apart from a $C_{8,18}$-alkyl or -acyl group in the molecule, comprise at least one free amino group and at least one —COOH or —SO$_3$H group and are capable of forming internal salts. Examples of suitable ampholytic surfactants are N-alkylglycines, N-alkylpropionic acids, N-alkylamino-butyric acids, N-alkyliminodipropionic acids, N-hydroxyethyl-N-alkylamido-propylglycines, N-alkyltaurines, N-alkylsarcosines, 2-alkylaminopropionic acids and alkylaminoacetic acids having in each case about 8 to 18 carbon atoms in the alkyl group.

Particularly preferred ampholytic surfactants are N-cocoalkylaminopropionate, cocoacylaminoethylaminopropionate and $C_{12/18}$-acylsarcosine. Besides the ampholytic ones, quaternary emulsifiers are also suitable, preference being given to those of the esterquat type, preferably methylquaternized difatty acid triethanolamine ester salts. Furthermore anionic emulsifiers which may be used are alkyl ether sulfates, monoglyceride sulfates, fatty acid sulfates, sulfosuccinates and/or ether carboxylic acids.

Suitable oil bodies are Guerbet alcohols based on fatty alcohols having 6 to 18, preferably 8 to 10, carbon atoms, esters of linear $C_6$-$C_{22}$-fatty acids with linear $C_6$-$C_{22}$-fatty alcohols, esters of branched $C_6$-$C_{13}$-carboxylic acids with linear $C_6$-$C_{22}$-fatty alcohols, esters of linear $C_6$-$C_{22}$-fatty acids with branched alcohols, in particular 2-ethylhexanol, esters of linear and/or branched fatty acids with polyhydric alcohols (such as, for example, propylene glycol, dimerdiol or trimertriol) and/or Guerbet alcohols, triglycerides based on $C_6$-$C_{10}$-fatty acids, liquid mono-/di-, triglyceride mixtures based on $C_6$-$C_{18}$-fatty acids, esters of $C_6$-$C_{22}$-fatty alcohols and/or Guerbet alcohols with aromatic carboxylic acids, in particular benzoic acid, esters of $C_2$-$C_{12}$-dicarboxylic acids with linear or branched alcohols having 1 to 22 carbon atoms or polyols having 2 to 10 carbon atoms and 2 to 6 hydroxyl groups, vegetable oils, branched primary alcohols, substituted cyclohexanes, linear $C_6$-$C_{22}$-fatty alcohol carbonates, Guerbet carbonates, esters of benzoic acid with linear and/or branched $C_6$-$C_{22}$- with linear and/or branched $C_6$-$C_{22}$-alcohols (e.g. Finsolv® TN), dialkyl ethers, ring-opening products of epoxidized fatty acid esters with polyols, silicone oils and/or aliphatic or naphthenic hydrocarbons. Further oil bodies which can be used are also silicone compounds, for example dimethylpolysiloxanes, methylphenylpolysiloxanes, cyclic silicones, and amino-, fatty acid-, alcohol-, polyether-, epoxy-, fluorine-, alkyl- and/or glycoside-modified silicone compounds, which may either be liquid or in resin form at room temperature. The oil bodies may be present in the compositions according to the invention in amounts of from 1 to 90% by weight, preferably 5 to 80% by weight and in particular 10 to 50% by weight, based on the composition.

According to a particularly preferred embodiment, the composition according to the invention comprises further UV photoprotective filters in the form of soluble compounds or other pigments.

Although it is possible, as already described above, to provide, with the help of the zinc oxide particles according to the invention, a sunscreen composition which achieves good UV absorption properties without further UV filter substances, it may be desired in individual cases to add further UV filter substances to the cosmetic composition or to the sunscreen composition. This may, for example, be necessary if particular emphasis is to be placed on filter performance. One or more further UV photoprotective filters can be added to the composition according to the invention.

In the case of the soluble compounds, UV photoprotective filters are understood as meaning organic substances which are able to absorb ultraviolet rays and give off the absorbed energy again in the form of longer-wave radiation, e.g. heat. The organic substances may be oil-soluble or water-soluble.

Oil-soluble UV-B filters which may be used are, for example, the following substances:

3-benzylidenecamphor and derivatives thereof, e.g. 3-(4-methylbenzylidene)camphor;

4-aminobenzoic acid derivatives, preferably 2-ethylhexyl 4-(dimethylamino)benzoate, 2-octyl 4-(dimethylamino)benzoate and amyl 4-(dimethylamino)benzoate;

esters of cinnamic acid, preferably 2-ethylhexyl 4-methoxycinnamate, propyl 4-methoxycinnamate, isoamyl 4-methoxycinnamate, isopentyl 4-methoxycinnamate, 2-ethylhexyl 2-cyano-3-phenylcinnamate (otocrylene);

esters of salicylic acid, preferably 2-ethylhexyl salicylate, 4-isopropylbenzyl salicylate, homomenthyl salicylate;

derivatives of benzophenone, preferably 2-hydroxy-4-methoxybenzophenone, 2-hydroxy-4-methoxy-4'-methylbenzophenone, 2,2'-dihydroxy-4-methoxybenzophenone;

esters of benzalmalonic acid, preferably 2-ethylhexyl 4-methoxybenzmalonate;

triazine derivatives, such as 2,4,6-trianilino(p-carbo-2'-ethyl-1'-hexyloxy)-1,3,5-triazine (octyltriazone) and dioctylbutamidotriazone (Uvasorb® HEB).

Propane-1,3-diones, such as, for example, 1-(4-tert-butylphenyl)-3-(4'-methoxyphenyl)propane-1,3-dione.

Suitable water-soluble substances are:

2-phenylbenzimidazole-5-sulfonic acid and alkali metal, alkaline earth metal, ammonium, alkylammonium, alkanolammonium and glucammonium salts thereof;

sulfonic acid derivatives of benzophenones, preferably 2-hydroxy-4-methoxybenzo-phenone-5-sulfonic acid and its salts;

sulfonic acid derivatives of 3-benzylidenecamphor, such as, for example, 4-(2-oxo-3-bornylidenemethyl)benzenesulfonic acid and 2-methyl-5-(2-oxo-3-bornylidene)sulfonic acid and salts thereof.

Particular preference is given to the use of esters of cinnamic acid, preferably 2-ethylhexyl 4-methoxycinnamate, isopentyl 4-methoxycinnamate, 2-ethylhexyl 2-cyano-3-phenylcinnamate (octocrylene).

Furthermore, the use of derivatives of benzophenone, in particular 2-hydroxy-4-methoxybenzophenone, 2-hydroxy-4-methoxy-4'-methylbenzophenone, 2,2'-dihydroxy-4-methoxybenzophenone, and the use of propane-1,3-diones, such as, for example, 1-(4-tert-butylphenyl)-3-(4-'methoxyphenyl)propane-1,3-dione is preferred.

Suitable typical UV-A filters are:

derivatives of benzoylmethane, such as, for example, 1-(4'-tert-butylphenyl)-3-(4'-methoxyphenyl)propane-1,3-dione, 4-tert-butyl-4'-methoxydibenzoylmethane or 1-phenyl-3-(4'-isopropylphenyl)propane-1,3-dione;

Aminohydroxy-substituted derivatives of benzophenones, such as, for example, N,N-diethylaminohydroxybenzoyl-n-hexylbenzoate.

The UV-A and UV-B filters can of course also be used in mixtures.

However, further photoprotective filters which may be used are also other insoluble pigments, e.g. finely disperse metal oxides and salts, such as, for example, titanium dioxide, iron oxide, aluminum oxide, cerium oxide, zirconium oxide, silicates (talc), barium sulfate and zinc stearate. The particles should here have an average diameter of less than 100 nm, preferably between 5 and 50 nm and in particular between 15 and 30 nm.

Besides the two abovementioned groups of primary photoprotective substances, it is also possible to use secondary photoprotective agents of the antioxidant type, which interrupt the photochemical reaction chain which is triggered when UV radiation penetrates into the skin. Typical examples thereof are superoxide dismutase, tocopherols (vitamin E) and ascorbic acid (vitamin C).

The total fraction of the photoprotective agents in the sunscreen composition according to the invention is usually 1 to 20% by weight, preferably 5 to 15% by weight. The composition according to the invention as such can comprise 1 to 95% by weight, preferably 5 to 80% by weight, and in particular 10 to 60% by weight, of water.

According to a particularly preferred embodiment, the cosmetic composition according to the invention also comprises care substances, further cosmetic active ingredients and/or auxiliaries and additives.

The further cosmetic active ingredients used are, in particular, skin moisturizers, antimicrobial substances and/or deodorizing or antiperspirant substances. This has the advantage that further desired effects can be achieved which contribute to the care or treatment of the skin or, for example, increase the wellbeing of the user of the cosmetic composition when using this composition.

For example, besides the carrier, the surface-modified zinc oxide, water and physiologically suitable solvents, the cosmetic composition may, inter alia, also comprise care constituents, such as, for example, oils, waxes, fats, refatting substances, thickeners, emulsifiers and fragrances. A high fraction of care substances is particularly advantageous for the topical prophylactic or cosmetic treatment of the skin.

It is particularly advantageous if, besides the animal and vegetable fats and oils, which in many cases likewise have a care effect, the composition also comprises further care components. The group of care active ingredients which can be used comprises, for example: fatty alcohols having 8-22 carbon atoms, in particular fatty alcohols of natural fatty acids; animal and vegetable protein hydrolysates, in particular elastin, collagen, keratin, milk protein, soja protein, silk protein, oat protein, pea protein, almond protein and wheat protein hydrolysates; vitamins and vitamin precursors, in particular those of vitamin groups A and B; mono-, di- and oligosaccharides; plant extracts; honey extracts; ceramides; phospholipids; vaseline, paraffin and silicone oils; fatty acid and fatty alcohol esters, in particular the monoesters of the fatty acids with alcohols having 3-24 carbon atoms. The vitamins, provitamins or vitamin precursors to be used in preference in the composition according to the invention include, inter alia: vitamins, provitamins and vitamin precursors from groups A, C, E and F, in particular 3,4-didehydroretinol, β-carotene (provitamin of vitamin A), ascorbic acid (vitamin C), and the palmitic esters, glucosides or phosphates of ascorbic acid, tocopherols, in particular α-tocopherol and its esters, e.g. the acetate, the nicotinate, the phosphate and the succinate; also vitamin F, which is understood as meaning essential fatty acids, particularly linoleic acid, linolenic acid and arachidonic acid;

Vitamin A and its derivatives and provitamins advantageously show a particular skin-smoothing effect.

The vitamins, provitamins or vitamin precursors of the vitamin B group or derivatives thereof and the derivatives of 2-furanone to be used in preference in the composition according to the invention include, inter alia:

Vitamin $B_1$, trivial name thiamine, chemical name 3-[(4'-amino-2'-methyl-5'-pyrimidinyl)methyl]-5-(2-hydroxyethyl)-4-methylthiazolium chloride. Preference is given to using thiamine hydrochloride in amounts of from 0.05 to 1% by weight, based on the total composition.

Vitamin $B_2$, trivial name riboflavin, chemical name 7,8-dimethyl-10-(1-D-ribityl)-benzo[g]pteridine-2,4(3H,10H)-dione. Riboflavin occurs in free form, for example, in whey, and other riboflavin derivatives can be isolated from bacteria and yeasts. A riboflavin stereoisomer which is likewise suitable according to the invention is lyxoflavin which can be isolated from fish meal or liver and which has a D-arabityl radical instead of the D-ribityl. Preference is given to using riboflavin or its derivatives in amounts of from 0.05 to 1% by weight, based on the total composition.

Vitamin $B_3$. This designation is often used for the compounds nicotinic acid and nicotinamide (niacinamide). The nicotinamide which is present in the compositions according to the invention preferably in amounts of from 0.05 to 1% by weight, based on the total composition, is preferred according to the invention.

Vitamin $B_5$ (pantothenic acid and panthenol). Preference is given to using panthenol. Panthenol derivatives which can be used according to the invention are, in particular, the esters and ethers of panthenol, and cationically derivatized panthenols. In a further preferred embodiment of the invention, derivatives of 2-furanone can also be used in addition to pantothenic acid or panthenol. Particularly preferred derivatives are the commercially available substances dihydro-3-hydroxy-4,4-dimethyl-2(3H)-furanone with the trivial name pantolactone (Merck), 4 hydroxymethyl-γ-butyrolactone (Merck), 3,3-dimethyl-2-hydroxy-γ-butyrolactone (Aldrich) and 2,5-dihydro-5-methoxy-2-furanone (Merck) with all stereoisomers being expressly included.

These compounds advantageously confer moisturizing and skin-calming properties on the cosmetic composition according to the invention.

The specified compounds of the vitamin $B_5$ type and the 2-furanone derivatives are present in the compositions according to the invention preferably in a total amount of from 0.05 to 10% by weight, based on the total composition. Total amounts of from 0.1 to 5% by weight are particularly preferred.

Vitamin $B_6$, which is not understood as meaning a uniform substance, but the derivatives of 5-hydroxymethyl-2-methylpyridin-3-ol which are known under the trivial names pyridoxine, pyridoxamine and pyridoxal. Vitamin $B_6$ is present in the compositions according to the invention preferably in amounts of from 0.0001 to 1.0% by weight, in particular in amounts of from 0.001 to 0.01% by weight.

Vitamin $B_7$ (biotin), also referred to as vitamin H or "skin vitamin". Biotin is (3aS,4S,6aR)-2-oxohexahydrothienol[3,4-d]imidazole-4-valeric acid. Biotin is present in the compositions according to the invention preferably in amounts of from 0.0001 to 1.0% by weight, in particular in amounts of from 0.001 to 0.01% by weight.

Panthenol, pantolactone, nicotinamide and biotin are very particularly preferred according to the invention.

Auxiliaries and additives are understood as meaning substances which are suitable for improving the esthetic, performance and/or cosmetic properties, such as, for example, coemulsifiers, organic solvents, superfatting agents, stabilizers, antioxidants, waxes or fats, consistency regulators, thickeners, tanning agents, vitamins, cationic polymers, biogenic active ingredients, preservatives, hydrotropes, solubilizers, dyes and fragrances.

For example, the following auxiliaries and additives may be used:

allantoin,
Aloe Vera,
bisabolol,
ceramides and pseudoceramides.

Antioxidants advantageously improve the stability of the compositions according to the invention. Antioxidants are, for example, amino acids (e.g. glycine, histidine, tyrosine, tryptophan) and derivatives thereof, imidazole and imidazole derivatives (e.g. urocanic acid), peptides, such as, for example, D,L-carnosine, D-carnosine, L-carnosine and derivatives thereof (e.g. anserine), carotenoids, carotenes (e.g. α-carotene, β-carotene, lycopene) and derivatives thereof, lipoic acid and derivatives thereof (e.g. dihydrolipoic acid), aurothioglucose, propylthiouracil and further thio compounds (e.g. thioglycerol, thiosorbitol, thioglycolic acid, thioredoxin, glutathione, cysteine, cystine, cystamine and the glycosyl, N-acetyl, methyl, ethyl, propyl, amyl, butyl, lauryl, palmitoyl, oleyl, γ-linoleyl, cholesteryl and glyceryl esters thereof, and salts thereof, dilauryl thiodipropionate, distearyl thiodipropionate, thiodipropionic acid and derivatives thereof (esters, ethers, peptides, lipids, nucleotides, nucleosides and salts), and sulfoximine compounds (e.g. buthionine sulfoximines, homocysteine sulfoximine, buthionine sulfones, penta-, hexa-, heptathionine sulfoximine) in very low tolerated doses (e.g. pmol/kg to pmol/kg), also metal chelating agents (e.g. α-hydroxy fatty acids, EDTA, EGTA, phytic acid, lactoferrin), α-hydroxy acids (e.g. citric acid, lactic acid, malic acid), humic acids, bile acid, bile extracts, gallic esters (e.g. propyl, octyl and dodecyl gallate), flavonoids, catechins, bilirubin, biliverdin and derivatives thereof, unsaturated fatty acids and derivatives thereof (e.g. γ-linolenic acid, linoleic acid, arachidonic acid, oleic acid), folic acid and derivatives thereof, hydroquinone and derivatives thereof (e.g. arbutin), ubiquinone and ubiquinol, and derivatives thereof, vitamin C and derivatives thereof (e.g. ascorbyl palmitate, stearate, dipalmitate, acetate, Mg ascorbyl phosphates, sodium and magnesium ascorbate, disodium ascorbyl phosphate and sulfate, potassium ascorbyl tocopheryl phosphate, chitosan ascorbate), isoascorbic acid and derivatives thereof, tocopherols and derivatives thereof (e.g. tocopheryl acetate, linoleate, oleate and succinate, tocophereth-5, tocophereth-10, tocophereth-12, tocophereth-18, tocophereth-50, tocophersolan), vitamin A and derivatives (e.g. vitamin A palmitate), the coniferyl benzoate of benzoin resin, rutin, rutinic acid and derivatives thereof, disodium rutinyl disulfate, cinnamic acid and derivatives thereof (e.g. ferulic acid, ethyl ferulate, caffeeic acid), kojic acid, chitosan glycolate and salicylate, butylhydroxytoluene, butylhydroxyanisol, nordihydroguaiacic acid, nordihydroguaiaretic acid, trihydroxybutyrophenone, uric acid and derivatives thereof, mannose and derivatives thereof, zinc and zinc derivatives (e.g. ZnO, ZnSO4), selenium and selenium derivatives (e.g. selenomethionine), stilbenes and stilbene derivatives (e.g. stilbene oxide, trans-stilbene oxide).

According to the invention, suitable derivatives (salts, esters, sugars, nucleotides, nucleosides, peptides and lipids) and mixtures of these specified active ingredients or plant extracts (e.g. teatree oil, rosemary extract and rosemarinic acid) which comprise these antioxidants can be used. As lipophilic, oil-soluble antioxidants from this group, preference is given to tocopherol and derivatives thereof, gallic esters, flavonoids and carotenoids, and butylhydroxytoluene/ anisol. As water-soluble antioxidants, amino acids, e.g. tyrosine and cysteine and derivatives thereof, and also tannins, in particular those of vegetable origin, are preferred. The total amount of antioxidants in the cosmetic compositions according to the invention is 0.001-20% by weight, preferably 0.05-10% by weight, in particular 0.1-5% by weight and very particularly preferably 0.1 to 2% by weight.

Triterpenes, in particular triterpenoic acids, such as ursolic acid, rosemarinic acid, betulinic acid, boswellic acid and byronolic acid, monomeric catechins, particularly catechin and epicatechin, leukoanthocyanidins, catechin polymers (catechin tannins) and gallotannins, thickeners, e.g. gelatins, plant gums such as agar agar, guar gum, alginates, xanthan gum, gum Arabic, karaya gum or carob seed grain, natural and synthetic clays and sheet silicates, e.g. bentonite, hectorite, montmorillonite or Laponite®, completely synthetic hydrocolloids, such as, for example, polyvinyl alcohol, and also Ca, Mg or Zn soaps of fatty acids, plant glycosides, structurants such as maleic acid and lactic acid, dimethyl isosorbide, alpha, beta and gamma-cyclodextrins, in particular for stabilizing retinol, solvents, swelling and penetration substances, such as ethanol, isopropanol, ethylene glycol, propylene glycol, propylene glycol monoethyl ether, glycerol and diethylene glycol, carbonates, hydrogencarbonates, guanidines, ureas and primary, secondary and tertiary phosphates perfume oils, pigments and dyes for coloring the composition, substances for adjusting the pH, e.g. α- and β-hydroxycarboxylic acids, complexing agents, such as EDTA, NTA, β-alaninediacetic acid and phosphoric acids, opacifiers, such as latex, styrene/PVP and styrene/acrylamide copolymers, pearlizing agents, such as ethylene glycol mono- and distearate and PEG-3 distearate, propellants, such as propane/butane mixtures, $N_2O$, dimethyl ether, $CO_2$ and air.

The addition of allantoin, bisabolol and/or Aloe Vera also in the form of extracts to the cosmetic compositions according to the invention also improves the skin-calming, moisturizing and skin care properties of the formulations and is therefore particularly preferred.

As further ingredients, the cosmetic composition according to the invention can comprise, in minor amounts, further surfactants which are compatible with the other ingredients.

Typical examples of anionic surfactants are soaps, alkylbenzenesulfonates, alkanesulfonates, olefinsulfonates, alkyl ether sulfonates, glycerol ether sulfonates, α-methyl ester sulfonates, sulfo fatty acids, alkyl sulfates, fatty alcohol ether sulfates, glycerol ether sulfates, hydroxy mixed ether sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids, such as, for example, acyl lactylates, acyl tartrates, acyl glutamates and acyl aspartates, alkyl oligoglucoside sulfates, protein fatty acid condensates (in particular wheat-based vegetable products) and alkyl (ether) phosphates.

If the anionic surfactants comprise polyglycol ether chains, these can have a conventional homolog distribution, but preferably have a narrowed homolog distribution.

Typical examples of nonionic surfactants are fatty alcohol polyglycol ethers, fatty acid polyglycol esters, fatty acid amide polyglycol ethers, fatty amine polyglycol ethers, alkoxylated triglycerides, mixed ethers and mixed formals, if appropriate partially oxidized alk(en)yl oligoglycosides and glucoronic acid derivatives, fatty acid N-alkylglucamides, protein hydrolysates (in particular wheat-based vegetable products), polyol fatty acid esters, sugar esters, sorbitan esters, polysorbates and amine oxides. If the nonionic surfactants comprise polyglycol ether chains, these may have a conventional homolog distribution, but preferably have a narrowed homolog distribution.

Typical examples of cationic surfactants are quaternary ammonium compounds and ester quats, in particular quaternized fatty acid trialkanolamine ester salts.

Typical examples of amphoteric and zwitterionic surfactants are alkylbetaines, alkyl-amidobetaines, aminopropionates, aminoglycinates, imidazoliniumbetaines and sulfobetaines.

According to a further particularly preferred embodiment, the cosmetic composition according to the invention is used as a sunscreen composition. The advantages resulting from this have already been described in detail.

The use of the zinc oxide dispersions according to the invention is, in particular, likewise possible in hair cosmetics such as shampoos, conditioners, rinses, hair tonics, hair gel, hair spray etc. In particular, leave-on products, which remain on the hair or the scalp following application, are particularly highly suitable. The zinc oxide applied in this way to the scalp and the hair can thus also act as a UV protectant and/or develop its skin-calming effect on the scalp.

According to a preferred embodiment of the cosmetic composition according to the invention, the cosmetic composition is thus applied topically to the surface of the body to be treated or to be protected. This application form is particularly advantageous since it is easy to handle, meaning that incorrect dosages are largely excluded. In addition, an additional care effect for the skin can also be achieved. If only parts of the body are exposed to solar radiation, the sunscreen composition can also only be applied in a targeted way to these parts of the body.

The present invention further provides the use of the metal oxides surface-modified according to the invention for UV protection. This is particularly advantageous since, due to the finely divided nature of, for example, the surface-modified zinc oxide and the good distribution, particularly high UV absorption is achieved.

The present invention further provides the use of the metal oxides surface-modified according to the invention, in particular of zinc oxide, as antimicrobial active ingredient. The use of these particles is particularly advantageous for this purpose since, on account of the finely divided nature of the particles and the large area resulting therefrom, the antimicrobial effect is greatly improved and, on the other hand, due to the good dispersion properties of the material, the zinc oxide is present in finely divided form. The zinc oxide can thus be used without problems in various application forms, such as, for example, creams, skin milk, lotions or tonics.

The present invention further provides a pharmaceutical composition which comprises a surface-modified metal oxide according to the invention. This pharmaceutical composition is notable for the fact that, due to the finely divided nature of the particles, the pharmaceutical effectiveness is greatly increased.

Moreover, the pharmaceutical composition according to the invention has the advantage that, due to the good long-term stability, already described above, of, for example, zinc oxide dispersions, it is possible to dispense with the addition of stabilizers which prevent separation. The compatibility of the pharmaceutical composition is thus additionally increased.

By reference to the examples below, the invention will be illustrated in more detail.

Preparation of Surface-Modified Zinc Oxide

EXAMPLE 1

500 ml of a 0.4 M NaOH solution which additionally comprised 2 g of a copolymer P of 94 mol % of vinylpyrrolidone and 6 mol % of sodium acrylate were heated to 40° C. and, over the course of 6 min, metered into 500 ml of a 0.2 M Zn(II) acetate solution, which was likewise heated to 40° C. The precipitate was stirred for 2 hours at 40° C. The precipitated product surface-modified using copolymer P was filtered off and dried at room temperature.

EXAMPLE 2

500 ml of a 0.4 M NaOH solution which additionally comprised 2 g of a copolymer P of 94.15 mol % of N-vinylcaprolactam and 5.85 mol % of sodium acrylate were heated to 40° C. and, over the course of 6 min, metered into 500 ml of a 0.2 M Zn(II) acetate solution, which was likewise heated to 40° C. The precipitate was stirred for 2 hours at 40° C. The precipitated product surface-modified using copolymer P was filtered off and dried at room temperature.

Examples of Cosmetic Formulations

General Procedure for Producing the Preparations According to the Invention as Emulsions Each of phases A and C were heated separately to about 85° C. Phase C and the metal oxide were then stirred into phase A with homogenization. Following brief after-homogenization, the emulsion was cooled to room temperature with stirring and bottled. All of the quantitative data refer to the total weight of the preparations.

EXAMPLE 3

Emulsion A, Comprising 3% by Weight of Uvinul® T150 and 4% by Weight of Zinc Oxide, Prepared as in Example 1

| Phase | % | INCI |
|---|---|---|
| A | 8.00 | Dibutyl Adipate |
|  | 8.00 | $C_{12}$-$C_{15}$ Alkyl Benzoate |
|  | 12.00 | Cocoglycerides |
|  | 1.00 | Sodium Cetearyl Sulfate |
|  | 4.00 | Lauryl Glucoside, Polyglyceryl-2 |
|  | 2.00 | Cetearyl Alcohol |
|  | 3.00 | Ethylhexyl Triazone (Uvinul ® T150) |
|  | 1.00 | Tocopheryl Acetate |
| B | 4.0 | Zinc Oxide |
| C | 3.00 | Glycerin |
|  | 0.20 | Allantoin |
|  | 0.30 | Xanthan Gum |
|  | 0.02 | Triethanolamine |
|  | ad 100 | Aqua dem. |

EXAMPLE 4

Emulsion B, Comprising 3% by Weight of Uvinul® T150, 2% by Weight of Uvinul® a Plus and 4% by Weight of Zinc Oxide, Prepared as in Example 1

| Phase | % | INCI |
|---|---|---|
| A | 8.00 | Dibutyl Adipate |
|  | 8.00 | C12-C15 Alkyl Benzoate |
|  | 12.00 | Cocoglycerides |
|  | 1.00 | Sodium Cetearyl Sulfate |
|  | 4.00 | Lauryl Glucoside, Polyglyceryl-2 |
|  | 2.00 | Cetearyl Alcohol |
|  | 3.00 | Ethylhexyl Triazone (Uvinul ® T150) |
|  | 1.00 | Tocopheryl Acetate |
|  | 2.00 | Diethylamino Hydroxybenzoyl Hexyl Benzoate (Uvinul ® A Plus) |
| B | 4.0 | Zinc Oxide |
| C | 3.00 | Glycerin |
|  | 0.20 | Allantoin |
|  | 0.30 | Xanthan Gum |
|  | 1.50 | Magnesium Aluminum Silicate |
|  | ad 100 | Aqua dem. |

EXAMPLE 5

Emulsion A, Comprising 3% by Weight of Uvinul® T150 and 4% by Weight of Zinc Oxide, Prepared as in Example 2

| Phase | % | INCI |
|---|---|---|
| A | 8.00 | Dibutyl Adipate |
|  | 8.00 | $C_{12}$-$C_{15}$ Alkyl Benzoate |
|  | 12.00 | Cocoglycerides |
|  | 1.00 | Sodium Cetearyl Sulfate |
|  | 4.00 | Lauryl Glucoside, Polyglyceryl-2 |
|  | 2.00 | Cetearyl Alcohol |
|  | 3.00 | Ethylhexyl Triazone (Uvinul ® T150) |
|  | 1.00 | Tocopheryl Acetate |
| B | 4.0 | Zinc Oxide |
| C | 3.00 | Glycerin |
|  | 0.20 | Allantoin |
|  | 0.30 | Xanthan Gum |
|  | 0.02 | Triethanolamine |
|  | ad 100 | Aqua dem. |

EXAMPLE 6

Emulsion B, Comprising 3% by Weight of Uvinul® T150, 2% by Weight of Uvinul® a Plus and 4% by Weight of Zinc Oxide, Prepared as in Example 2

| Phase | % | INCI |
|---|---|---|
| A | 8.00 | Dibutyl Adipate |
|  | 8.00 | C12-C15 Alkyl Benzoate |
|  | 12.00 | Cocoglycerides |
|  | 1.00 | Sodium Cetearyl Sulfate |
|  | 4.00 | Lauryl Glucoside, Polyglyceryl-2 |
|  | 2.00 | Cetearyl Alcohol |
|  | 3.00 | Ethylhexyl Triazone (Uvinul ® T150) |

-continued

| Phase | % | INCI |
|---|---|---|
|  | 1.00 | Tocopheryl Acetate |
|  | 2.00 | Diethylamino Hydroxybenzoyl Hexyl Benzoate (Uvinul ® A Plus) |
| B | 4.0 | Zinc Oxide |
| C | 3.00 | Glycerin |
|  | 0.20 | Allantoin |
|  | 0.30 | Xanthan Gum |
|  | 1.50 | Magnesium Aluminum Silicate |
|  | ad 100 | Aqua dem. |

We claim:

1. A process for the preparation of a surface-modified nanoparticulate metal oxide, where the metal is chosen from the group consisting of aluminum, cerium, iron, titanium, zinc and zirconium, by
   a. precipitation of the metal oxide from an aqueous or alcoholic solution of one of its metal salts,
   b. separating off the precipitated metal oxide from the aqueous or alcoholic reaction mixture and
   c. subsequent drying of the metal oxide,
   wherein the precipitation of the metal oxide in process step a. takes place in the presence of a copolymer P which comprises, as monomers,
   A) 1 to 99 mol % of a N-vinylamide and
   B) 99 to 1 mol % of a monomer comprising, per molecule, one free-radically polymerizable $\alpha,\beta$-ethylenically unsaturated double bond and one anionogenic and/or anionic group,
   with the proviso that the copolymer P must comprise no further monomers chosen from the group consisting of $C_8$-$C_{30}$-alkyl esters of monoethylenically unsaturated $C_3$-$C_8$-carboxylic acids, N-alkyl- or N,N-dialkyl-substituted amides of acrylic acid or of methacrylic acid with $C_8$-$C_{18}$-alkyl radicals, or vinyl esters of aliphatic $C_8$-$C_{30}$-carboxylic acids.

2. The process according to claim 1, wherein the precipitation takes place in the presence of a copolymer P comprising, as component A), 50 to 99 mol % of N-vinylpyrrolidone and, as component B), 1 to 50 mol % of acrylic acid.

3. The process according to claim 2, wherein the metal salts are metal halides, acetates, sulfates or nitrates.

4. The process according to claim 2, wherein the precipitation takes place at a temperature in the range from 20° C. to 100° C.

5. The process according to claim 2, wherein the precipitation takes place at a pH in the range from 3 to 12.

6. The process according to claim 2 for the preparation of surface-modified nanoparticulate zinc oxide.

7. A surface-modified nanoparticulate metal oxide, obtainable by a process according to claim 2.

8. The process according to claim 1, wherein the metal salts are metal halides, acetates, sulfates or nitrates.

9. The process according to claim 8, wherein the precipitation takes place at a temperature in the range from 20° C. to 100° C.

10. The process according to claim 3, wherein the precipitation takes place at a pH in the range from 3 to 12.

11. The process according to claim 8 for the preparation of surface-modified nanoparticulate zinc oxide.

12. The process according to claim 1, wherein the precipitation takes place at a temperature in the range from 20° C. to 100° C.

13. The process according to claim 1, wherein the precipitation takes place at a pH in the range from 3 to 12.

14. The process according to claim 1 for the preparation of surface-modified nanoparticulate zinc oxide.

15. The process according to claim 14, wherein the precipitation of the zinc oxide in process step a. takes place from an aqueous solution of zinc(II) chloride, zinc(II) nitrate or zinc(II) acetate at a temperature in the range from 25 to 40° C. and a pH in the range from 7 to 11 in the presence of the copolymer P.

16. A surface-modified nanoparticulate metal oxide, obtainable by a process according to claim 1.

17. The surface-modified metal oxide according to claim 16, wherein the metal oxide particles have an average primary particle diameter of from 5 to 10000 nm.

18. The method for producing cosmetic preparations comprising the surface-modified nanoparticulate metal oxides as defined according to claim 16.

19. The method of producing according to claim 18 for producing cosmetic sunscreen preparations.

20. A cosmetic preparation comprising surface-modified nanoparticulate metal oxides defined according to claim 16.

* * * * *